(12) United States Patent
Sullivan et al.

(10) Patent No.: US 7,663,746 B2
(45) Date of Patent: *Feb. 16, 2010

(54) METHOD AND APPARATUS FOR SCANNING, STITCHING AND DAMPING MEASUREMENTS OF A DOUBLE SIDED METROLOGY INSPECTION TOOL

(75) Inventors: Paul J. Sullivan, Sunnyvale, CA (US); Geroge Kren, Los Altos Hills, CA (US); Rodney C. Smedt, Los Gatos, CA (US); Hans J. Hansen, Pleasanton, CA (US); David W. Shortt, Milpitas, CA (US); Daniel Ivanov Kavaldjiev, Santa Clara, CA (US); Christopher F. Bevis, Mountain View, CA (US)

(73) Assignee: KLA-Tencor Techologies Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/287,290

(22) Filed: Oct. 7, 2008

(65) Prior Publication Data

US 2009/0040514 A1  Feb. 12, 2009

Related U.S. Application Data

(63) Continuation of application No. 11/366,108, filed on Mar. 1, 2006, now Pat. No. 7,436,506, which is a continuation of application No. 10/759,764, filed on Jan. 16, 2004, now Pat. No. 7,009,696, which is a continuation of application No. 10/165,344, filed on Jun. 7, 2002, now Pat. No. 6,686,996, which is a continuation of application No. 09/335,673, filed on Jun. 18, 1999, now Pat. No. 6,414,752.

(51) Int. Cl.
  *G01N 21/84* (2006.01)
(52) U.S. Cl. .............. 356/237.4; 356/237.5; 356/237.2

(58) Field of Classification Search ... 356/237.2–237.5; 250/559.45; 382/141, 145–147
See application file for complete search history.

(56) References Cited

U.S. PATENT DOCUMENTS

| | | | |
|---|---|---|---|
| 4,335,313 | A | 6/1982 | Kreuzer et al. |
| 4,659,172 | A | 4/1987 | Cavan |
| 4,999,511 | A | 3/1991 | Kohno |
| 5,086,477 | A | 2/1992 | Yu et al. |

(Continued)

FOREIGN PATENT DOCUMENTS

EP 544957 6/1993

(Continued)

*Primary Examiner*—L. G Lauchman
(74) *Attorney, Agent, or Firm*—Smyrski Law Group, A P.C.

(57) ABSTRACT

A system for inspecting specimens such as semiconductor wafers is provided. The system provides scanning of dual-sided specimens using a damping arrangement which filters unwanted acoustic and seismic vibration, including an optics arrangement which scans a first portion of the specimen and a translation or rotation arrangement for translating or rotating the specimen to a position where the optics arrangement can scan the remaining portion(s) of the specimen. The system further includes means for stitching the scans together, thereby providing both damping of the specimen and the need for smaller and less expensive optical elements.

20 Claims, 6 Drawing Sheets

U.S. PATENT DOCUMENTS

| | | |
|---|---|---|
| 5,359,407 A | 10/1994 | Suzuki et al. |
| 5,381,225 A | 1/1995 | Kohno |
| 5,481,202 A | 1/1996 | Frye, Jr. |
| 5,495,097 A | 2/1996 | Katz et al. |
| 5,712,890 A | 1/1998 | Spivey et al. |
| 5,790,932 A | 8/1998 | Komaki et al. |
| 5,917,590 A | 6/1999 | Greve |
| 5,970,168 A | 10/1999 | Montesanto et al. |
| 6,113,056 A | 9/2000 | Armstrong |
| 6,204,917 B1 | 3/2001 | Smedt |
| 6,252,705 B1 | 6/2001 | Lo et al. |
| 6,414,752 B1 | 7/2002 | Sullivan et al. |
| 7,009,696 B2 | 3/2006 | Sullivan et al. |

FOREIGN PATENT DOCUMENTS

| | | |
|---|---|---|
| WO | 9727452 | 7/1997 |

METHOD AND APPARATUS FOR SCANNING, STITCHING AND DAMPING MEASUREMENTS OF A DOUBLE SIDED METROLOGY INSPECTION TOOL

This application is a continuation of U.S. patent application Ser. No. 11/366,108, filed Mar. 1, 2006 now U.S. Pat. No. 7,436,506, entitled "Method and Apparatus for Scanning, Stitching, and Damping Measurements of a Double Sided Metrology Inspection Tool," inventors Paul J. Sullivan, et al., which is a continuation of U.S. patent application Ser. No. 10/759,764, filed Jan. 16, 2004, entitled "Method and Apparatus for Scanning, Stitching, and Damping Measurements of a Double Sided Metrology Inspection Tool," inventors Paul J. Sullivan, et al., now U.S. Pat. No. 7,009,696, issued Mar. 7, 2006. which is a continuation of U.S. patent application Ser. No. 10/165,344, filed Jun. 7, 2002, entitled "Method and Apparatus for Scanning, Stitching, and Damping Measurements of a Double Sided Metrology Inspection Tool," inventors Paul J. Sullivan, et al., now U.S. Pat. No. 6,686,996, issued Feb. 3, 2004, which is a continuation of U.S. patent application Ser. No. 09/335,673, filed Jun. 18, 1999, entitled "Method and Apparatus for Scanning, Stitching, and Damping Measurements of a Double Sided Metrology Inspection Tool," inventors Paul J. Sullivan, et al., now U.S. Pat. No. 6,414,752, issued Jul. 2, 2002, all of which are hereby incorporated by reference.

BACKGROUND OF THE INVENTION

1. Field of the Invention

The present invention relates generally to the field of optical imaging and more particularly to systems for sub-aperture data imaging of double sided interferometric specimens, such as semiconductor wafers.

2. Description of the Related Art

The progress of the semiconductor industry over the last years has resulted in a sharp increase in the diameters of semiconductor wafers as base material for chip production for economic and process technical reasons. Wafers having diameters of 200 and 300 millimeters are currently processed as a matter of course.

At present manufacturers and processors of wafers in the 200 and 300 mm range do not have a wide range of measuring devices available which enable inspection of particular geometric features, namely flatness, curvature, and thickness variation, with sufficient resolution and precision.

As scanning of specimens has improved to the sub-aperture range, the time required to perform full specimen inspection for a dual-sided specimen has also increased. Various inspection approaches have been employed, such as performing an inspection of one side of the specimen, inverting the specimen, and then inspecting the other side thereof. Such a system requires mechanically handling the specimen, which is undesirable. Further, the act of inspecting the specimen has generally required binding the specimen, which can cause deformation at the edges of the specimen, increase defects at the edge, or cause bending of the specimen during inspection.

One method for inspecting both sides of a dual sided specimen is disclosed in PCT Application PCT/EP/03881 to Dieter Mueller and currently assigned to the KLA-Tencor Corporation, the assignee of the current application. The system disclosed therein uses a phase shifting interferometric design which facilitates the simultaneous topography measurement of both sides of a specimen, such as a semiconductor wafer, as well as the thickness variation of the wafer. A simplified drawing of the Mueller grazing incidence interferometer design is illustrated in FIG. 1A. The system of FIG. 1A uses a collimated laser light source 101 along with a lensing arrangement 102 to cause grazing of light energy off the surface of both sides of the specimen 103 simultaneously. A second lensing arrangement 104 then provides focusing of the resultant light energy and a detector 105 provides for detection of the light energy.

The design of FIG. 1A is highly useful in performing topographical measurements for both sides of a dual-sided specimen in a single measurement cycle, but suffers from particular drawbacks. First, the system requires minimum specimen movement during measurement, which can be difficult due to vibration in the surrounding area and vibration of the specimen itself. Further, the inspection can be time consuming and requires highly precise light energy application and lensing, which is expensive. The specimen must be free standing and free of edge forces, and the incidence geometry during inspection must be unimpeded. Access must be preserved under all incidence angles. These factors provide mechanical challenges for successfully supporting the specimen; excessive application of force at a minimum number of points may deform the specimen, while numerous contact points impede access and require exact position to avoid specimen deformation or bending during inspection. Further, edge support of the specimen has a tendency to cause the specimen to act like a membrane and induce vibration due to slight acoustic or seismic disturbances. This membrane tendency combined with the other problems noted above have generally been addressed by including most components of the system within an enclosure that minimizes ambient vibrations, which adds significant cost to the system and does not fully solve all vibration problems.

The cost of lenses sized to accommodate inspection of a full wafer in the arrangement shown in FIG. 1A are highly expensive, and generally have the same diameter as the diameter of the specimen, generally 200 or 300 millimeters depending on the application. Full aperture decollimating optics, including precision lenses, gratings, and beamsplitters used in a configuration for performing full inspection of a 300 millimeter specimen are extremely expensive, generally costing orders of magnitude more than optical components half the diameter of the wafer.

It is therefore an object of the current invention to provide a system for performing a single measurement cycle inspection of a dual-sided specimen having dimensions up to and greater than 300 millimeters.

It is a further object of the present invention to provide a system for inspection of dual-sided specimens without requiring an excessive number of binding points and simultaneously allowing free access for inspection of both sides of the specimen.

It is a further object of the current invention to provide for the single measurement cycle inspection of a dual-sided specimen while minimizing the tendency for the specimen to behave as a membrane and minimize any acoustic and/or seismic vibrations associated with the inspection apparatus and process.

It is still a further object of the present invention to accomplish all of the aforesaid objectives at a relatively low cost, particularly in connection with the collimating and decollimating optics and any enclosures required to minimize acoustic and seismic vibrations.

SUMMARY OF THE INVENTION

The present invention is a system for inspecting a wafer, including inspecting both sides of a dual sided wafer or specimen. The wafer is mounted using a fixed three point mounting arrangement which holds the wafer at a relatively fixed position while simultaneously minimizing bending and stress. Light energy is transmitted through a lensing arrangement employing lenses having diameter smaller than the specimen, such as half the size of the specimen, arranged to cause light energy to strike the surface of the wafer and subsequently pass through second collimating lens where detection and observation is performed.

The system further includes at least one damping bar, where the number of damping bars depends on the wafer repositioning arrangement. The effect of the damping bar is to perform viscous film damping, or VFD, of the non-measured surface of the specimen to minimize the effects of vibration in accordance with VFD, or the Bernoulli principle. Each damping bar is positioned to be within close proximity of the surface to be damped. The proximity between any damping bar and the surface of the wafer is preferably less than 0.5 millimeters, and spacing of 0.25 and 0.33 may be successfully employed. Smaller gaps provide problems when warped specimens are inspected. One embodiment of the current invention employs a damping bar to cover slightly less than half of the specimen when in scanning position.

Mounting for the wafer uses a three point kinematic mount. The mounting points include clips having spherical or semispherical tangentially mounted contacts, mounted to a support plate and arranged to be substantially coplanar, where the clips are adjustable to provide for slight irregularities in the shape of the wafer. The adjustability of the contact points provide the ability to hold the wafer without a stiff or hard connection, which could cause bending or deformation, as well as without a loose or insecure connection, which could cause inaccurate measurements.

Light energy is conducted through a beam waveguide and then strikes a deviation mirror, is redirected onto a parabolic collimation mirror by two further deviation mirrors. The deviation mirrors are oriented at an angle of 90° relative to each other. The parallel light beam P reflected from the parabolic mirror reaches a beam splitter through the two deviation mirrors.

The beam splitter is formed as a first diffraction grating and is arranged in the apparatus in a vertical direction. The parallel light beam P strikes the diffraction grating in a perpendicular direction. A beam collector in the form of a second diffraction grating is disposed from the first diffraction grating and parallel thereto. Behind the beam collector two decollimation lenses are arranged at equal level. The light beams leaving the decollimation lenses are each deflected and focused onto two CCD cameras through various deviation mirror pairs and to an optical imaging system.

The beam splitter is supported transversely to the optical axis and includes a piezoelectric actuating element for shifting the phase of the parallel light beam P by displacing the diffraction grating.

A wafer or specimen to be measured is held on a holding device such that both plane surfaces are arranged in vertical direction parallel to the light beam P. The wafer is supported substantially at its vertical edge so that both surfaces are not substantially contacted by the support post and are freely accessible to the interferometric measurement.

A receiving device may be provided. Further, a reference apparatus may be provided which comprises a reference body having at least one plane surface. The reference body can be introduced into the light path between the first diffraction grating and the second diffraction grating in place of the semiconductor wafer or specimen to be measured by means of a traveller with a linear guide. The reference body is held so that its plane surface is arranged in vertical direction parallel to the undiffracted light beam P.

Modifications of the imaging apparatus and method are possible. A body having two precisely plane parallel surfaces may be used for the reference body, whereby both surfaces are measured simultaneously. However, the embodiment having a single plane surface of the reference body is more suitable.

In one arrangement, a light source initially emits light energy and strikes two mirror surfaces, which each direct light energy through a first collimating lens and simultaneously strike the two surfaces of the specimen. Light energy is thereupon directed through a second pair of collimating lens and to a second pair of mirrors, toward a focusing element arrangement, and a detector. A translation surface or mounting surface holding the contact points and wafer or specimen is fastened to a translation stage, which provides translation or sliding of the specimen within and into the lensing/imaging arrangement. The system first performs an inspection of one portion of the specimen, and the translation stage and wafer are repositioned or translated such as by driving the translating stage so that another portion of the wafer is within the imaging path. The other portion of the wafer is then imaged, and both two sided images of the wafer are "stitched" together.

Other means for presenting the remaining portion of wafer or specimen may be employed, such as rotating the wafer mechanically or manually, or keeping the wafer fixed and moving the optics and imaging components. Alternately, scanning may be performed using multiple two-sided inspections of the module, such as three, four, or five or more scans of approximate thirds, quarters, or fifths, and so forth of the specimen. While multiple scans require additional time and thus suffer from increased throughput, such an implementation could provide for use of smaller optics, thereby saving overall system costs.

In a two phase scan of a dual sided specimen, at least 50 percent of the surface must be scanned in each phase of the scan. It is actually preferred to scan more than 50 percent, such as 55 percent, in each scan to provide for a comparison between scans and the ability to "stitch" the two scans together.

Scanning and stitching involves determining the piston and tilt of the specimen during each scan, adjusting each scan for the piston and tilt of said scan, and possibly performing an additional stitching procedure. Additional stitching procedures include, but are not limited to, curve fitting the points between the overlapping portions of the two scans using a curve fitting process, replacing overlapping pixels with the average of both data sets, or weighting the averaging in the overlapping region to remove edge transitions by using a trapezoidal function, half cosine function, or other similar mathematical function. Background references are preferably subtracted to improve the stitching result. If significant matching between the scans is unnecessary, such as in the case of investigating for relatively large defects, simply correcting for tilt and piston may provide an acceptable result. However, in most circumstances, some type of curve fitting or scan matching is preferred, if not entirely necessary.

These and other objects and advantages of the present invention will become apparent to those skilled in the art from the following detailed description of the invention and the accompanying drawings.

DETAILED DESCRIPTION OF THE INVENTION

Figure 1A:
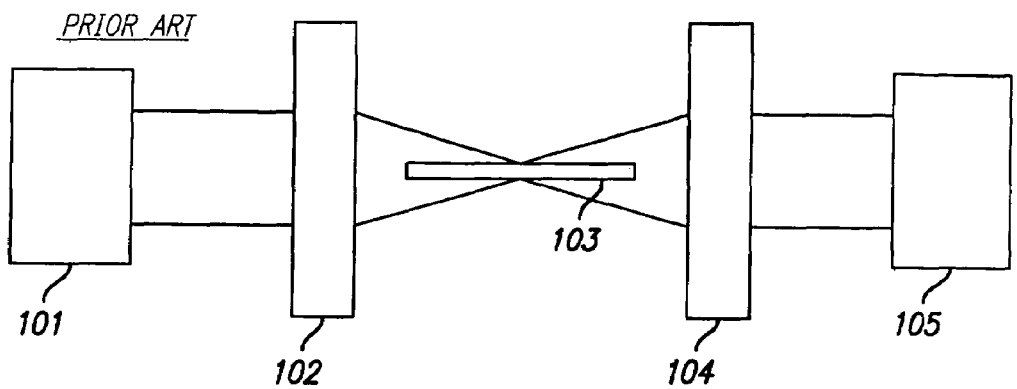
FIG. 1A illustrates the general concept of the predecessor Mueller system for inspecting both sides of a semiconductor wafer or specimen when said specimen is oriented in a substantially "vertical" orientation.
Figure 1B:
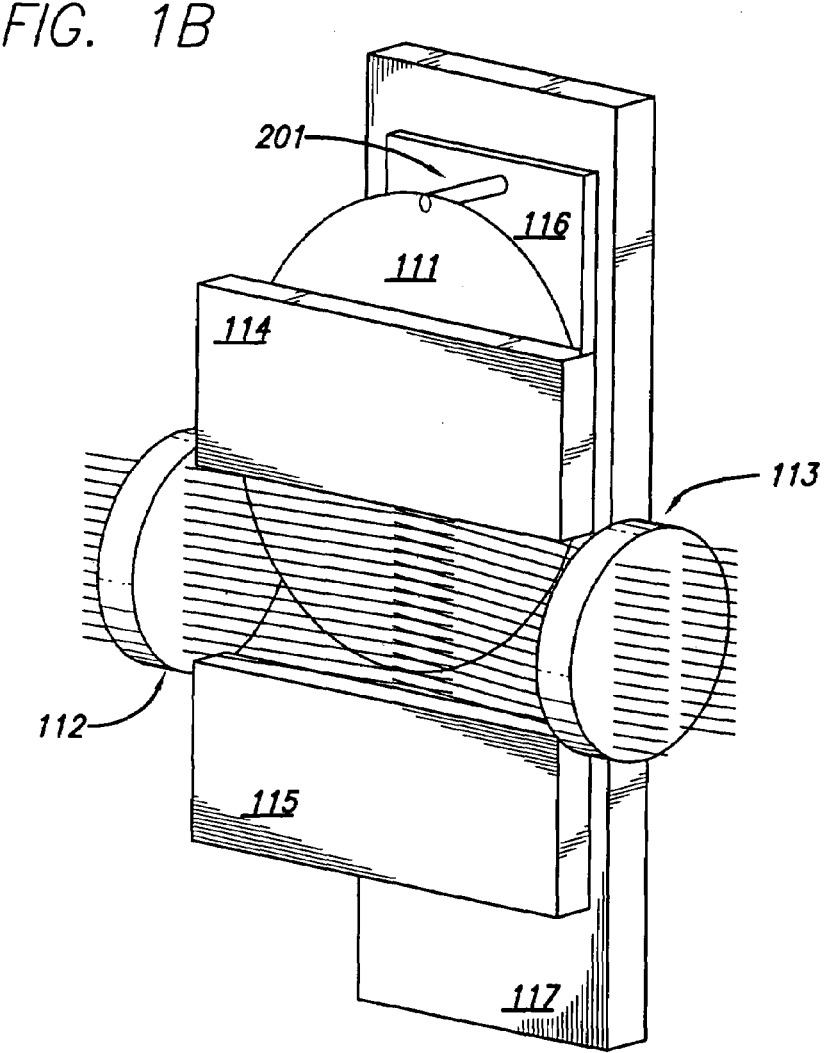
FIG. 1B illustrates a first embodiment of the present invention, including the damping bar and dual sided lensing arrangement.
Figure 2:
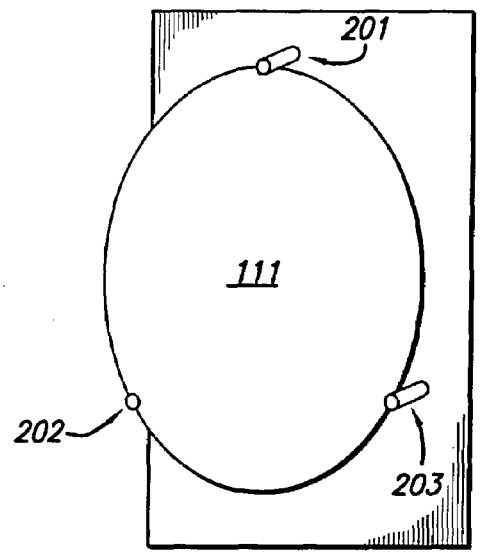
FIG. 2 presents the mounting points of the wafer or specimen.

FIG. 1B illustrates a first embodiment of the present invention, specifically one for scanning both sides of a dual-sided wafer or specimen 111. According to FIG. 1B, the wafer 111 is mounted using a fixed three point mounting arrangement which is shown in FIG. 2. The three point mounting arrangement serves to hold the wafer 111 at a relatively fixed position while simultaneously minimizing any bending or stressing of the dual-sided wafer. Light energy is transmitted through first collimating lens 112 which is arranged to cause light energy to strike the surface of the wafer 111 and subsequently pass through second collimating lens 113 where detection and observation is performed. As may be appreciated by examining FIG. 1B, the diameter of both first collimating lens 112 and second collimating lens 113 are significantly smaller than the diameter of the specimen or wafer 111, and incident light strikes only a portion of the surface of wafer 111. Not shown in the illustration of FIG. 1B is that while light energy is striking the surface of wafer 111 visible in the arrangement shown, light energy simultaneously passes through first collimating lens 112 and strikes the reverse side of the wafer 111, not shown in FIG. 1B. Light energy passes from the reverse side of the specimen 111 through second collimating lens 113.

The arrangement further includes an upper damping bar 114 and a lower damping bar 115. In the arrangement shown in FIG. 1B, the upper damping bar 114 covers approximately one half of the specimen 111, specifically the half not being inspected. The effect of the damping bar is to damp the non-measured surface of the specimen 111 to minimize the effects of vibration. Damping in this arrangement is based on VFD, or the Bernoulli principle, wherein the upper damping bar 114 in the arrangement shown is brought to within close proximity of the surface to be damped. The proximity between either damping bar 114 or 115 and the surface of the wafer is preferably less than 0.5 millimeters, and spacing of 0.25 and 0.33 may be successfully employed. The problem associated with providing smaller gaps between either damping bar 114 or 115 and the surface of wafer 111 is that any warping of the wafer may cause the bar to contact the surface. For this reason, and depending on the wafer surface, gaps less than 0.10 millimeters are generally undesirable. Further, gaps greater than 1.0 millimeters do not produce a desirable damping effect, as the Bernoulli principle does not result in sufficient damping in the presence of gaps in excess of 1.0 millimeter.

The gap between the specimen 111 and upper damping bar 114 or lower damping bar 115 restricts airflow between the specimen and the damping bar and damps vibration induced in the specimen. Each damping bar is generally constructed of a stiff and heavy material, such as a solid steel member. Overall dimensions are important but not critical in that the damping bar should cover a not insignificant portion of the wafer 111. Coverage of less than 20 percent of the wafer tends to minimize the overall damping effect on the wafer, but does provide some level of damping.

The illumination of only a portion of the wafer 111 provides for using smaller lenses than previously performed. In the embodiment shown in FIG. 1B, the preferred size of the first collimating lens 112 and second collimating lens 113 is approximately 4.4 inches where the wafer 111 is 300 millimeters in diameter. In such an arrangement, the damping bars 114 and 115 are approximately 4.5 inches wide. Length of the damping bars depends on the mode of wafer movement, as discussed below.

As shown in FIG. 2, the mounting for the wafer 111 is preferably using a three point kinematic mount, where the three points 201, 202, and 203 represent spherical or semispherical contacts tangential to one another. Points 201, 202, and 203 are small clips having spherical or semi-spherical tangentially mounted contacts, mounted to a support plate such as mounting plate 116 to be substantially coplanar, with adjustable clips to provide for slight irregularities in the shape of the wafer 111. The spherical or semispherical components should be sufficiently rigid but not excessively so, and a preferred material for these components is ruby. The adjustability of points 201, 202, and 203 provide an ability to hold the wafer 111 without a stiff or hard connection, which could cause bending or deformation, as well as without a loose or insecure connection, which could cause inaccurate measurements. In FIG. 1B, two lower kinematic mount points 202 and 203 (not shown) support the lower portion of the wafer 111, while the upper portion is supported by mount point and clip 201. The points 201, 202 and 203 are therefore stiff enough to mount the wafer or specimen 111 and prevent "rattling" but not so stiff as to distort the wafer. The spherical or semispherical contact points are generally known to those of skill in the mechanical arts, particularly those familiar with mounting and retaining semiconductor wafers. The combination of clamping in this manner with the Bernoulli damping performed by the damping bars 114 and 115 serves to minimize acoustic and seismic vibration.

Figure 7:
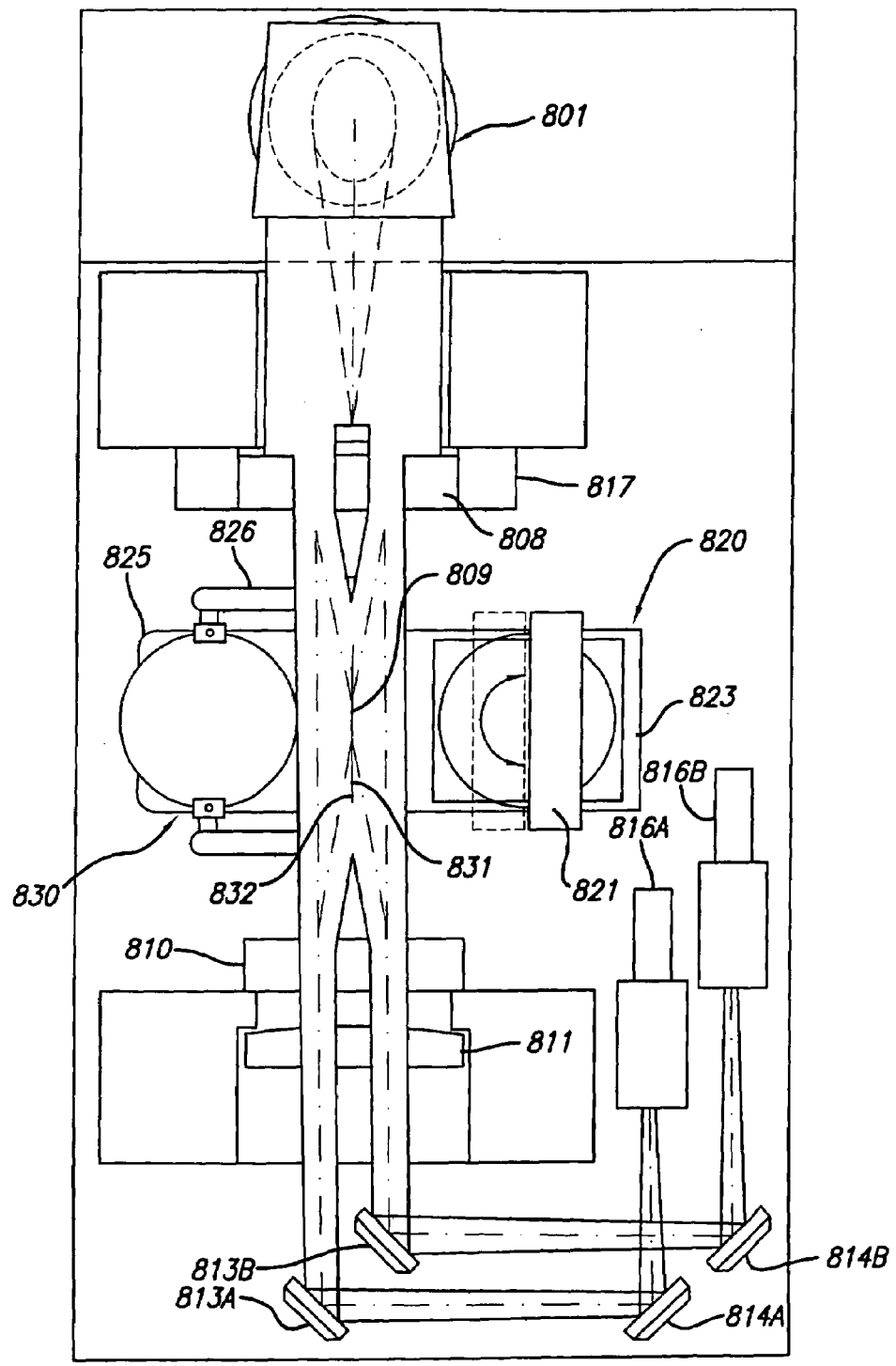
FIG. 7 presents a conceptual schematic representation of the components and optics necessary to perform dual sided imaging of a semiconductor wafer.
Figure 8:
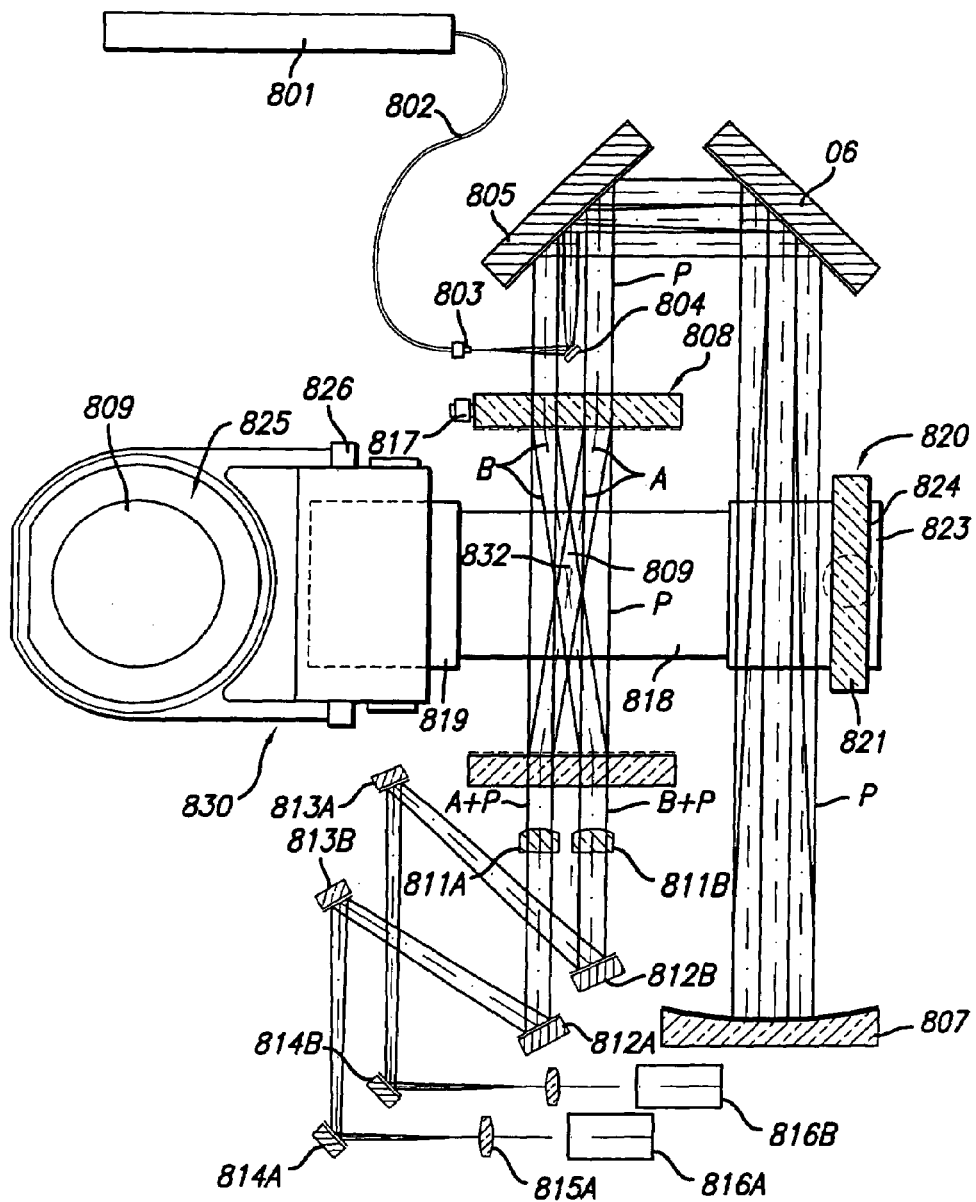
FIG. 8 is a top view of the components and optics which shows the path of light energy.

Simultaneous imaging of both sides of the specimen is performed in accordance with PCT Application PCT/EP/03881 to Dieter Mueller, currently assigned to the KLA-Tencor Corporation, the assignee of the current application. The entirety of PCT/EP/03881 is incorporated herein by reference. This imaging arrangement is illustrated in FIGS. 7 and 8. As shown in FIGS. 7 and 8, the light energy directing apparatus employed in the current invention comprises a light source in the form of a laser 801. The light emitted from the laser 801 is conducted through a beam waveguide 802. The light produced by the laser 801 emerges at an end 803 of the beam waveguides 802 so that the end 803 acts as a punctual light source. The emerging light strikes a deviation mirror 804 wherefrom it is redirected onto a collimation mirror 807 in the form of a parabolic mirror by two further deviation mirrors 805 and 806. Deviation mirrors 805 and 806 are oriented at an angle of 90° relative to each other. The parallel light beam P reflected from the parabolic mirror 807 reaches a beam splitter 808 through the two deviation mirrors 805 and 806.

The beam splitter 808 is formed as a first diffraction grating and is preferably a phase grid. The beam splitter 808 is arranged in the apparatus in a vertical direction and the parallel light beam P strikes the diffraction grating in a perpendicular direction. A beam collector 810 in the form of a second diffraction grating is disposed from the first diffraction grating 808 and parallel thereto. Behind the beam collector 810 two decollimation lenses 811 are arranged at equal level and the light beams leaving these decollimation lenses are each deflected and focused onto two CCD cameras 816, through deviation mirror pairs 812A and 812B, 813A and 813B, and 814A and 814B, and to an optical imaging system 15.

The beam splitter 808 is supported transversely to the optical axis and further comprises a piezoelectric actuating element 817 for shifting the phase of the parallel light beam P by displacing the diffraction grating.

A holding device 830, for example in the form of a support post, is provided centrally between the first diffraction grating and the second diffraction grating. A wafer or specimen 809 to be measured is held on the holding device 830 such that both plane surfaces 831 and 832 are arranged in vertical direction parallel to the light beam P. The wafer 809 is supported by the support post substantially at its vertical edge 833 only so that both surfaces 831 and 832 are not substantially contacted by the support post and are freely accessible to the interferometric measurement.

Moreover, a receiving device (830, 825) may be provided for the wafer 809 to be measured. The wafer can be inserted into the receiving device in a horizontal position. By means of a tilting device 826 the wafer 809 may be tilted from its horizontal position into the vertical measuring position, and the wafer 809 may be transferred, by means of a positionable traveller, into the light path between the first diffraction grating and the second diffraction grating so that the surfaces 809 and 832 to be measured are aligned substantially parallel to the undiffracted light beam P and in a substantially vertical direction.

Furthermore, a reference apparatus 820 may be provided which comprises a reference body 821 having at least one plane surface 824. The reference body 821 can be introduced into the light path between the first diffraction grating 808 and the second diffraction grating 810 in place of the semiconductor wafer or specimen 809 to be measured by means of a traveller 823 with a linear guide 818. The reference body 821 is held so that its plane surface 824 is arranged in vertical direction parallel to the undiffracted light beam P. The reference body 821 can be turned by 180° in its mounting around an axis parallel to its surface 824.

In operation the wafer or specimen 809 to be measured is first inserted into the wafer receiving device 825. The surfaces 831 and 832 are horizontally arranged. By means of the tilting device and of the traveller 819 the wafer to be measured is brought into the holding device 830 where it is arranged so that the surfaces 831 and 832 are vertical. A diffraction of the parallel light beam P striking the first diffraction grating 808 of the beam splitter produces partial light beams A, B, whereby the partial light beam A having a positive diffraction angle strikes the one surface 831 of the wafer 809 and is reflected thereat, whereas the partial light beam B with a negative diffraction angle strikes the other surface 832 of the wafer and is reflected thereat. The 0-th diffraction order of the parallel light beam P passes through the first diffraction grating 808 and is not reflected at the surfaces 831 and 832 of the wafer 809. This partial light beam P serves as references beam for interference with the reflected wave fronts of the beams A and B. In the second diffraction grating 810, the beam collector and the reflected partial light beams A and B are each combined again with the reference beam P of the 0-th diffraction order and focused, in the form of two partial light beams A+P and B+P onto the focal planes of the CCD cameras 816 through decollimation lenses 811 and deviation mirrors 812, 813 and 814 as well as positive lenses 815.

During the exposure of the surfaces the phase of the parallel light beam P is repeatedly shifted by 90° and 120° by displacing the diffraction grating. This produces phase shifted interference patterns. The defined shift of the interference phase produced by the phase shifter 817 is evaluated to determine whether there is a protuberance or a depression in the measured surfaces 831 and 832 the two digitized phase patterns are subtracted from each other.

A calibration using the reference body 821 can be performed before each measurement of a wafer 809. The reference body 821 is introduced into the beam path between the first diffraction grating 808 and the second diffraction grating 810. The known plane surface 824 is measured. Subsequently the reference body 821 is turned by 180° and the same surface 824 is measured as a second surface.

Figure 3:
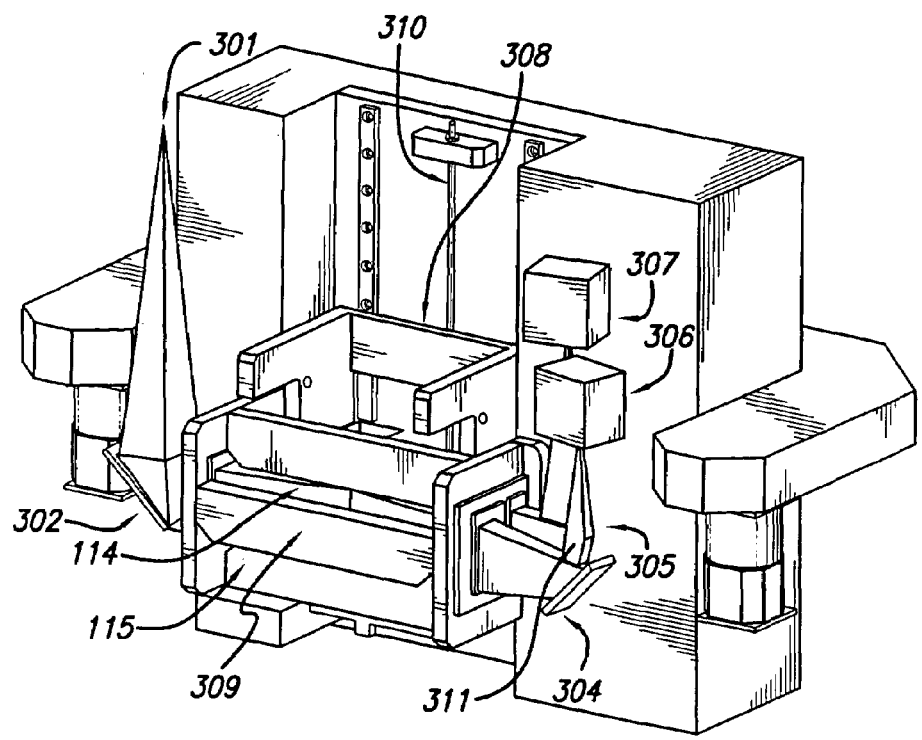
FIG. 3 illustrates a measurement module for use in connection with translating the wafer and performing multiple scans in the presence of multiple damping bars.

FIG. 3 illustrates the measurement model without a wafer or specimen present. From FIG. 3, light source 301 initially emits light energy and is focused to strike first mirror surface 302 and second mirror surface 303 (not shown). Each of these two mirror surfaces direct light energy through first collimating lens 112 (not shown in this view) and light energy strikes the two surfaces of specimen 111 (also not shown) simultaneously. After striking the two surfaces of specimen 111, light energy is directed through second collimating lens 113 (also not shown in FIG. 2) and to third mirror 304 and fourth mirror 305, which direct light energy toward focusing element 306 and detector 307. Imaging arm 311 represents the light image path from third mirror 304 toward focusing element 306. Focusing elements and sensors are those known in the art, and may include a lensing arrangement, such as multiple lenses, and a CCD or other imaging sensor. Other implementations of focusing element 306 and detector or sensor 307 are possible while still within the scope of the current invention.

From FIG. 1B, the specimen 111 is mounted to three points, including point 201, which are fixedly mounted to mounting surface 116. Mounting surface 116 may be fixedly mounted to translation surface 117. Either translation surface 117 or mounting surface 116 is fastened to translation stage 308, which provides translation or sliding of the mounting surface 116 and specimen 111 within and into the arrangement shown in FIG. 3. The arrangement may further include translation surface 117 depending on the application. Translation stage 308 permits the arrangement of FIG. 1B, specifically wafer or specimen 111, points 201, 202, and 203, mounting surface 116, and translation surface 117, to move up and down in a relatively limited range, as described below. In such an arrangement employing translation surface 117, the translation surface and the mounting surface along with the contact points are positioned within the measurement module 300, preferably by affixing the translation surface 117 to the translation stage 308. Specimen 111 is then physically located between damping bars 114 and 115, as well as proximate damping bar 309 and fastened to points 201, 202, and 203. Once the specimen 111 has been adequately fastened to points 201, 202, and 203, an inspection of the lower portion of the wafer is initiated. After completing an adequate inspection, i.e. an inspection of one portion of the specimen 111 with acceptable results, the translation stage 308 and ultimately the wafer are repositioned or translated such as by driving the translating stage 308 along track 310 such that another portion of the wafer 111, such as the remaining approximately half of specimen 111 is within the imaging path. The other portion of the wafer is then imaged, and both of the two sided images of the wafer surface are "stitched" together.

The damping bars may have varying size while still within the scope of the current invention, as discussed above. In FIG. 3, the damping bars are affixed to end pieces 310 and 311, but any type of mounting will suffice as long as the gap spacing described above and the ability to perform scans on desired portions of the wafer is available.

As may be appreciated, other means for presenting the remaining portion of wafer or specimen 111 may be employed, such as rotating the wafer by hand by releasing contact with the points and rotating the wafer manually. Alternately, a mechanical rotation of the specimen may occur, such as by rotatably mounting the mounting surface 116 on the translating surface 117 while providing for two locking positions for the mounting surface 116. In other words, the arrangement of wafer 111, points 201, 202, and 203, and mounting surface 116 would initially fixedly engage translation surface 117. On completion of a first inspection scan of a portion of specimen 111, wafer 111, points 201, 202, and 203, and mounting surface 116 would be unlocked from translation surface 117 and be mechanically or manually rotated vertically on an axis perpendicular to translation surface 117. The wafer and associated hardware rotate 180 degrees to a second locking position, wherein the surface would lock and a second inspection scan would commence. During this rotation scheme, damping bars and impediments would be mechanically or manually removed to prevent contact with mounting points 201, 202, and 203. The various components, particularly mounting surface 116, are sized to accommodate rotation within the measurement module 300 without contacting the translation stage or other module components.

Alternately, scanning may be performed using multiple two-sided inspections of the module, such as three, four, or five scans of approximate thirds, quarters, or fifths of the specimen. While multiple scans require additional time and thus suffer from increased throughput, such an implementation could provide for use of smaller optics, thereby saving on system costs. Numerous sub-aperture scans may be performed by a system similar to that illustrated in FIG. 3 while still within the scope of the current invention.

Figure 4A:
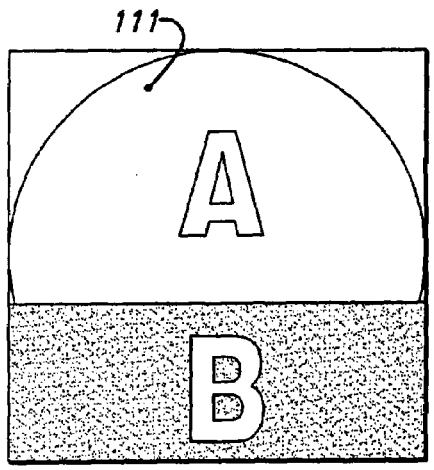
FIG. 4A shows the first position of the wafer or specimen relative to a damping bar when a rotational scanning and stitching procedure is performed on approximately half the wafer surface.
Figure 4B:
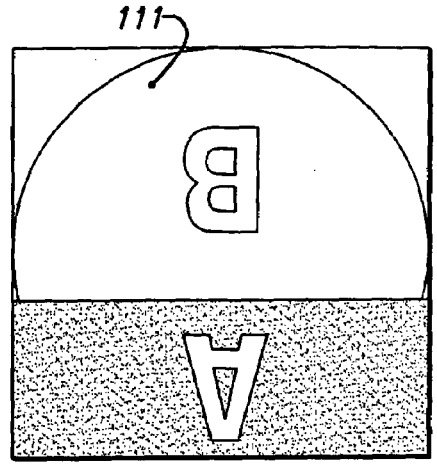
FIG. 4B is the second position of the wafer or specimen relative to a damping bar when a rotational scanning and stitching procedure is performed on the other approximately half of the wafer surface.

FIGS. 4A and 4B illustrate a rotational scanning arrangement of the wafer or specimen 111. As may be appreciated, in a two phase scan of a dual sided specimen, at least 50 percent of the surface must be scanned in each phase of the scan. It is actually preferred to scan more than 50 percent, such as 55 percent, in each scan to provide for a comparison between scans and the ability to "stitch" the two scans together. In such an arrangement, as shown in FIG. 4A, over 50 percent of the surface is scanned initially, shown as portion A of the surface 111. Portion B is obscured by one of the damping bars. After the initial scan phase, the specimen 111 is rotated manually or mechanically to the position illustrated in FIG. 4B. Approximately 55 percent of the wafer surface, both front and back, are scanned during this second phase. This provides an overlap of five percent of the wafer, and comparisons between these overlap portions provides a reference for stitching the scans together. In FIG. 4B, the A portion of the wafer is obscured by the damping bar.

Figure 5A:
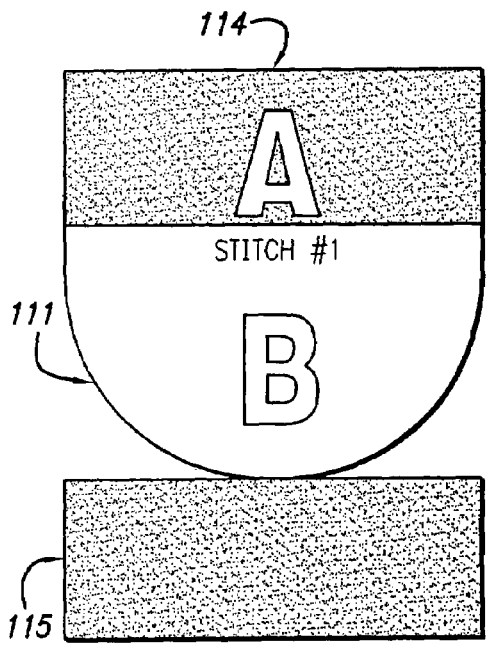
FIG. 5A shows the first position of the wafer or specimen relative to a damping bar arrangement when a translational scanning and stitching procedure is performed on approximately half the wafer surface.
Figure 5B:
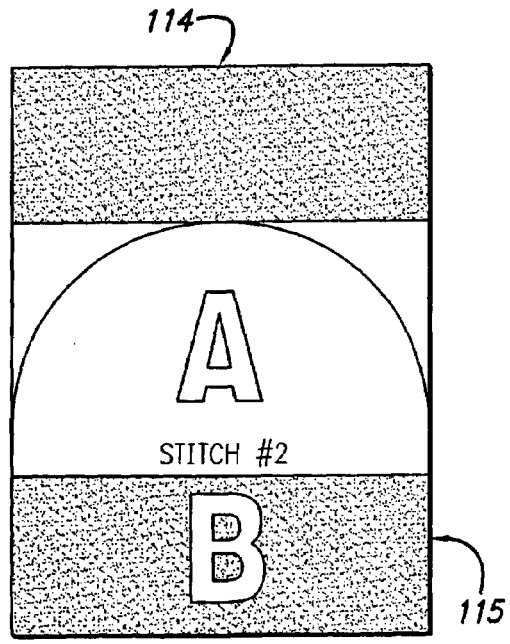
FIG. 5B is the second position of the wafer or specimen relative to a damping bar arrangement when a translational scanning and stitching procedure is performed on the other approximately half of the wafer surface.

Alternately, as in the arrangement shown in FIG. 3, the wafer or specimen 111 may be translated vertically and two or more separate scans performed. As shown in FIGS. 5A and 5B, a portion of the wafer 111 is positioned between two damping bars, such as damping bars 114 and 115, and the portion marked "B" in FIG. 5A is scanned. As shown therein, greater than 50 percent of the specimen 111 is scanned so that the overlapping portion may be stitched with the second scan. After the initial scan, the wafer is translated to a position as shown in FIG. 5B. Portion "A" of FIG. 5B is then scanned, while the lower damping bar covers much of section "B." The overlapping portions of the two scans are then stitched together to provide a full representation of the surface, and again such a scan is dual-sided.

From FIGS. 4A, 4B, 5A, and 5B, it should be apparent that a single damping bar is required if the specimen 111 is to be rotated as shown in FIGS. 4A and 4B, while two damping bars are required if the wafer 111 is to be translated, as shown in FIGS. 5A and 5B. Note that due to measurement setup, an arbitrary piston or DC offset and tilt will be applied to each of the measurements, indicating that some correction is required prior to or during stitching to obtain an accurate surface representation.

Figure 6:
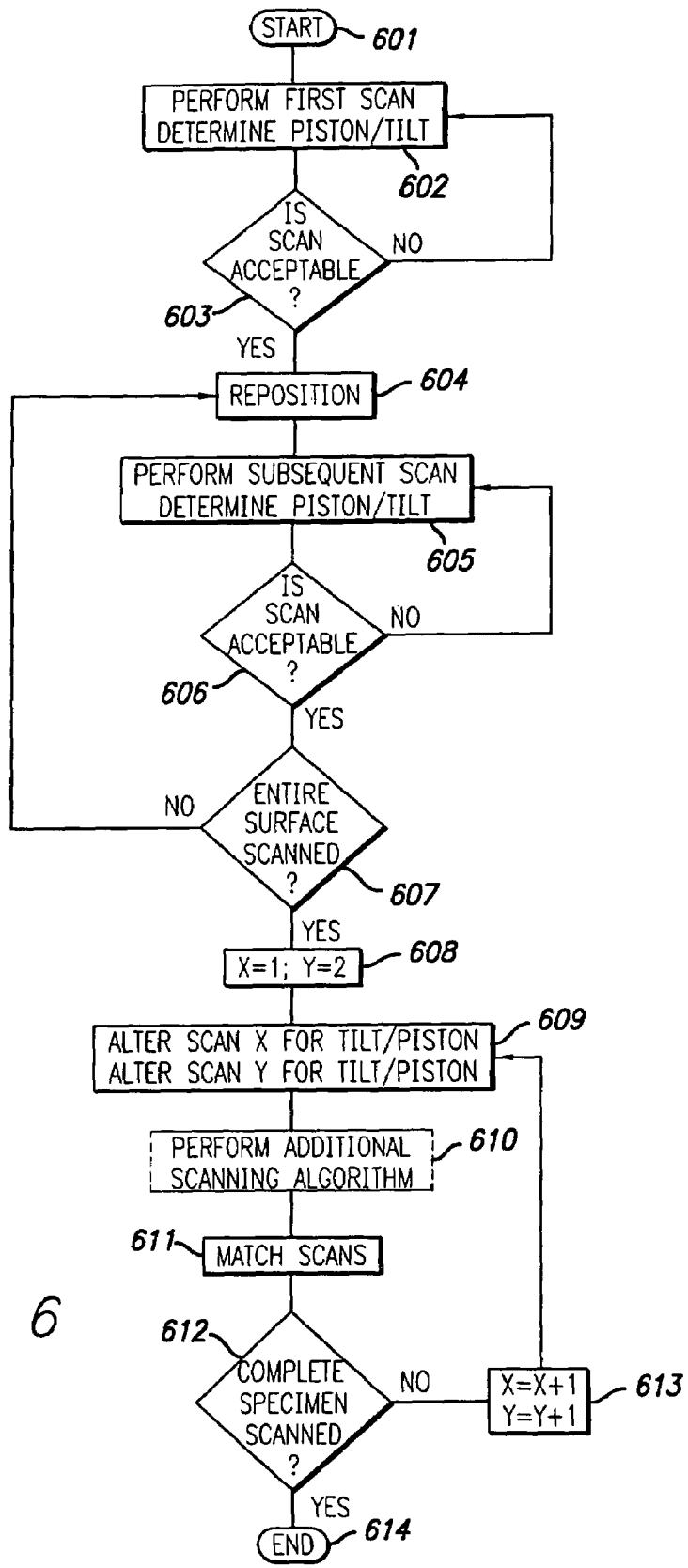
FIG. 6 represents an algorithm for performing the scanning and stitching according to the present invention.

FIG. 6 illustrates a general scanning and stitching algorithm for use in accordance with the invention described herein. The algorithm begins in step 601 and performs the first scan in step 602, as well as determining the piston and tilt of the specimen 111. The algorithm evaluates whether the scan is acceptable in step 603, either performed by an operator actually evaluating the scan or a mechanical comparison with a known or previous scan. If the scan is acceptable, the algorithm proceeds to step 604 where the wafer is repositioned to the next location. If the scan is not acceptable, the wafer is rescanned in its original position. Piston and tilt may be recomputed, but as the wafer has not moved this is not necessary. Once the wafer has been repositioned in step 604, a subsequent scan is performed in step 605 and the tilt and piston computed for the new orientation. The acceptability of the scan is evaluated in step 606, and if unacceptable, the scan performed again. The piston and tilt again do not need to be recalculated. Once the scan is mechanically or visually deemed acceptable, the algorithm determines whether the entire surface has been scanned in step 607. If the entire surface has not been scanned, the wafer is again repositioned and the remaining scans performed in accordance with the illustrated steps. If the entire surface has been scanned, the algorithm sets x equal to one and y equal to 2 in step 608. In step 609 the system alters scan x for tilt and piston and separately alters scan y for its respective tilt and piston. At this point scans x and y are neutrally positioned and may be stitched together. Step 610 is an optional step of performing an additional stitching procedure. Additional stitching procedures include, but are not limited to, curve fitting the points between the overlapping portions of the two scans using a curve fitting process, replacing overlapping pixels with the average of both data sets, or weighting the averaging in the overlapping region to remove edge transitions by using a trapezoidal function, half cosine function, or other similar mathematical function. Background references are preferably subtracted to improve the stitching result. If significant matching between the scans is unnecessary, such as in the case of investigating for relatively large defects, simply correcting for tilt and piston may provide an acceptable result, and step 610 need not be performed. However, in most circumstances, some type of curve fitting or scan matching is necessary. Scans are matched and stitched in step 611. Such stitching algorithms should preferably be performed using a computing device, such as a microprocessor (not shown).

Step 612 evaluates whether the complete wafer has been stitched together. If it has not, the algorithm proceeds to increment x and y in step 613 and perform additional stitching of the remaining portions. If the complete wafer has been stitched, the algorithm exits in step 614.

Based on the disclosure presented above and in particular in connection with that shown in FIG. 3, the wafer 111 is generally repositioned while the inspection energy source and optics remain fixed. While this implementation provides distinct advantages in setup time for performing multiple dual-sided wafer scans, it is to be understood that the light source and associated optics and detector may be slidably or rotationally mounted while the wafer remains fixed. In the configuration illustrated in FIG. 3, source 301, support elements 310 and 311, damping bars 114 and 115, damping bar 309, the four mirrors 302, 303, 304, and 305, focusing element 306, and detector 307 may be mounted to a single surface and fixedly positioned relative to one another, and translated or rotated about the wafer. Alternately, the components may be translated either together or individually to perform subsequent scans of the wafer or specimen 111.

While the invention has been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. An inspection system, comprising:
a damped edge mounted semiconductor wafer damped by a damping element having no contact with the edge mounted damped semiconductor wafer;
an inspection illuminator configured to direct light energy toward the damped edge mounted semiconductor wafer; and
an inspection sensor configured to receive reflected light energy from the damped edge mounted semiconductor wafer.

2. The system of claim 1, further comprising:
a positioning arrangement to fixedly maintain the damped edge mounted semiconductor wafer; and
a repositioning arrangement for repositioning said positioning arrangement relative to the inspection illuminator.

3. The system of claim 2, wherein said inspection sensor receives light energy from said damped edge mounted semiconductor wafer and provides multiple partial representations thereof, said system further comprising a stitching device to stitch multiple partial representations together.

4. The system of claim 1, wherein said damping element comprises a damping bar spaced apart from the damped edge mounted semiconductor wafer by an air gap.

5. The system of claim 2, wherein said repositioning arrangement comprises translating means for translating said damped edge mounted semiconductor wafer.

6. The system of claim 3, wherein said inspection illuminator directs light energy to a predetermined portion of said semiconductor wafer unobstructed by the damping element.

7. The system of claim 2, wherein the positioning arrangement comprises a three point kinematic mount, wherein all points of the three point kinematic mount are substantially tangentially oriented.

8. An inspection method, comprising:
providing an edge mounted damped semiconductor wafer;
directing light energy toward the edge mounted damped semiconductor wafer; and
receiving light energy reflected from the edge mounted damped semiconductor wafer.

9. The method of claim 8, wherein said light energy is directed by an illuminator, the method further comprising:
fixedly maintaining the edge mounted damped semiconductor wafer in an edge mounted orientation using a positioning arrangement; and
periodically repositioning said positioning arrangement relative to the illuminator.

10. The method of claim 9, wherein said receiving comprises receiving light energy from said edge mounted damped semiconductor wafer and establishing multiple representations thereof, said method further comprises stitching the multiple representations together.

11. The method of claim 8, wherein said edge mounted damped semiconductor wafer is damped by a damping element spaced from the edge mounted damped semiconductor wafer by an air gap.

12. The method of claim 9, wherein said repositioning comprises translating said edge mounted damped semiconductor wafer.

13. The method of claim 10, wherein said directing comprises directing light energy to a predetermined unobstructed portion of said edge mounted damped semiconductor wafer.

14. An inspection method, comprising:
providing an edge mounted damped semiconductor wafer, said edge mounted damped semiconductor damped by a damping element having no contact with the edge mounted damped semiconductor wafer;
emitting light energy toward the edge mounted damped semiconductor wafer; and
receiving light energy reflected from the edge mounted damped semiconductor wafer, wherein light energy received via said receiving is employed to inspect the edge mounted damped semiconductor wafer.

15. The method of claim 14, wherein said emitting occurs using a light emitter, the method further comprising:
fixedly maintaining the edge mounted damped semiconductor wafer using a positioning arrangement; and
selectively repositioning said positioning arrangement relative to the light emitter.

16. The method of claim 15, further comprising using received light energy from said receiving to provide a representation of the edge mounted damped semiconductor wafer.

17. The method of claim 16, further comprising performing multiple scans and stitching multiple edge mounted damped semiconductor wafer representations together.

18. The method of claim 15, wherein selectively repositioning comprises translating said edge mounted damped semiconductor wafer.

19. The method of claim 16, wherein said emitting comprises directing light energy to a predetermined portion of said edge mounted damped semiconductor wafer.

20. The method of claim 15, wherein the positioning arrangement comprises a three point kinematic mount, wherein all points of the three point kinematic mount are substantially tangentially oriented.

* * * * *